(12) United States Patent
Grychowski et al.

(10) Patent No.: US 7,849,853 B2
(45) Date of Patent: Dec. 14, 2010

(54) VENTILATOR CIRCUIT AND THE METHOD FOR THE USE THEREOF

(75) Inventors: Jerry R. Grychowski, Lake Zurich, IL (US); Martin P. Foley, London (CA); Michael S. Dunn, Toronto (CA)

(73) Assignee: Trudell Medical International, London (CA)

( * ) Notice: Subject to any disclaimer, the term of this patent is extended or adjusted under 35 U.S.C. 154(b) by 889 days.

(21) Appl. No.: 10/774,751

(22) Filed: Feb. 9, 2004

(65) Prior Publication Data

US 2005/0039746 A1 Feb. 24, 2005

Related U.S. Application Data

(60) Provisional application No. 60/446,487, filed on Feb. 11, 2003.

(51) Int. Cl.
| | |
|---|---|
| *F16K 31/02* | (2006.01) |
| *A61M 11/00* | (2006.01) |
| *A61M 15/00* | (2006.01) |
| *A61M 15/08* | (2006.01) |
| *A61M 16/00* | (2006.01) |
| *A62B 7/10* | (2006.01) |

(52) U.S. Cl. .............. 128/204.23; 128/200.14; 128/200.16; 128/200.18; 128/200.21; 128/200.22; 128/203.12; 128/203.18; 128/203.24; 128/203.25; 128/203.29; 128/205.12

(58) Field of Classification Search ............ 128/200.14, 128/200.22, 200.23, 203.12, 203.25, 204.11, 128/204.12, 200.16, 200.18, 200.21, 203.18, 128/203.24, 203.29, 205.12

See application file for complete search history.

(56) References Cited

U.S. PATENT DOCUMENTS 3,028,873 A 4/1962 Kindred (Continued)

FOREIGN PATENT DOCUMENTS

CA 2 210 721 7/1996

(Continued)

OTHER PUBLICATIONS

International Search Report for PCT/IB2004/000333 filed Feb. 10, 2004.

(Continued)

*Primary Examiner*—Patricia M Bianco
*Assistant Examiner*—Nihir Patel
(74) *Attorney, Agent, or Firm*—Brinks Hofer Gilson & Lione

(57) ABSTRACT

A ventilator circuit for use in administering medication to a patient includes a chamber housing defining an interior space and having an input end and an output end and a one-way inhalation valve positioned upstream of the interior space. The one-way inhalation valve is operative to permit a flow of medication into the interior space of the chamber housing. An inhalation conduit communicates with the output end of the chamber and is adapted to transmit the medication to the patient. An exhaust conduit is connected to the inhalation conduit and a one-way exhaust valve is located in the exhaust conduit. The one-way exhaust valve is adapted to prevent a backflow of gas from the exhaust conduit into the inhalation conduit. A method of administering a medication to a patient is also provided.

15 Claims, 3 Drawing Sheets

U.S. PATENT DOCUMENTS

| | | | |
|---|---|---|---|
| 3,726,274 A | | 4/1973 | Bird et al. |
| 4,534,343 A | | 8/1985 | Nowacki et al. |
| 4,803,977 A | * | 2/1989 | Kremer, Jr. ............... 600/3 |
| 4,938,210 A | | 7/1990 | Shene |
| 5,002,048 A | | 3/1991 | Makiej, Jr. |
| 5,005,572 A | | 4/1991 | Raemer et al. |
| 5,012,804 A | | 5/1991 | Foley et al. |
| 5,178,138 A | * | 1/1993 | Walstrom et al. ...... 128/200.23 |
| 5,357,946 A | | 10/1994 | Kee et al. |
| 5,666,946 A | | 9/1997 | Langenback |
| 5,693,944 A | | 12/1997 | Rich |
| 5,816,240 A | | 10/1998 | Komesaroff |
| 5,848,587 A | | 12/1998 | King |
| 6,014,972 A | | 1/2000 | Sladek |
| 6,039,042 A | | 3/2000 | Sladek |
| 6,269,810 B1 | * | 8/2001 | Brooker et al. .......... 128/203.12 |
| 6,279,574 B1 | * | 8/2001 | Richardson et al. .... 128/204.18 |
| 6,390,091 B1 | * | 5/2002 | Banner et al. .......... 128/204.21 |
| 6,435,177 B1 | | 8/2002 | Schmidt et al. |
| 6,527,011 B1 | * | 3/2003 | Mantz ........................ 137/848 |
| 6,581,600 B2 | * | 6/2003 | Bird ....................... 128/205.24 |
| 6,805,118 B2 | * | 10/2004 | Brooker et al. ......... 128/203.12 |
| 6,886,561 B2 | * | 5/2005 | Bayron et al. .......... 128/205.24 |
| 7,201,167 B2 | | 4/2007 | Fink et al. |
| 2002/0069870 A1 | * | 6/2002 | Farmer ................. 128/200.22 |
| 2002/0104531 A1 | | 8/2002 | Malone |
| 2003/0131844 A1 | | 7/2003 | Kumar et al. |
| 2004/0003808 A1 | | 1/2004 | Fuhrman et al. |
| 2005/0005929 A1 | | 1/2005 | Snyder et al. |
| 2005/0217666 A1 | | 10/2005 | Fink et al. |
| 2005/0217667 A1 | | 10/2005 | Dhuper et al. |
| 2005/0247312 A1 | | 11/2005 | Davies |
| 2005/0274378 A1 | | 12/2005 | Bonney et al. |

FOREIGN PATENT DOCUMENTS

| | | |
|---|---|---|
| CA | 2 329 126 | 10/1999 |
| CA | 2 354 561 | 6/2000 |
| CA | 2 493 078 | 2/2004 |
| CA | 2 515 593 | 8/2004 |
| CA | 2 424 731 | 10/2004 |
| EP | 0 281 650 A1 | 9/1988 |
| EP | 0 972 534 A2 | 1/2000 |
| EP | 0 972 534 A3 | 1/2000 |
| GB | 750 152 A | 6/1953 |
| WO | WO 2004/011071 | 2/2004 |
| WO | WO 2004/071549 A2 | 8/2004 |
| WO | WO 2006/026237 A | 3/2006 |
| WO | WO 2006/114699 A2 | 11/2006 |
| WO | WO 2007/030162 A2 | 3/2007 |

OTHER PUBLICATIONS

Written Opinion of the International Searching Authority for PCT/IB2004/000333 filed Feb. 10, 2004.

"The Use of Aerosolized Medicines in Neonates," Cynthia H. Cole, M.D., M.P.H., Neonatal Respiratory Diseases, vol. 10, No. 4; Associates in Medical Marketing Co., Inc., Newtown, PA.; 2000, 6 pages.

"A Dose-ranging study to assess the effect of inhaled corticosteroids in ventilated preterm neonates.," Drs. Vibhuti Shah and Edmond Kelly, Mount Sinai Hospital, and Dr. Michael Dunn, Sunnybrook and Women's College Health Sciences Center, date unknown, 27 pages.

Written Opinion in International Application No. PCT/IB2006/001027, dated Sep. 21, 2006, 8 pages.

International Search Report in International Application No. PCT/IB2006/001027, dated Sep. 21, 2006, 6 pages.

Office Action and PTO-892 in U.S. Appl. No. 11/410,270 filed Apr. 24, 2006, Grychowski et al., dated Jan. 20, 2010, 14 pages.

* cited by examiner

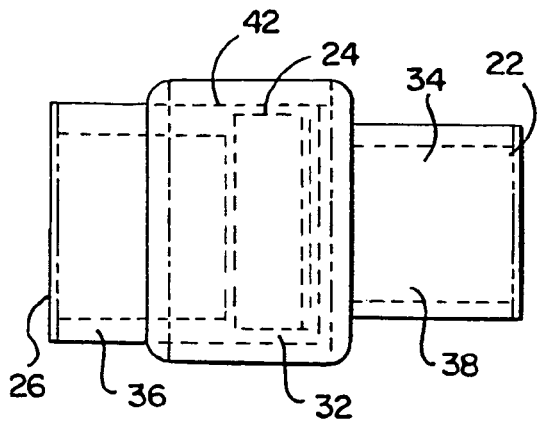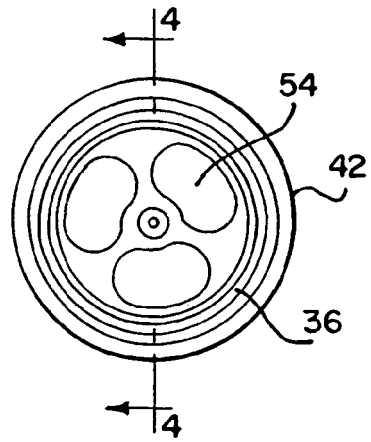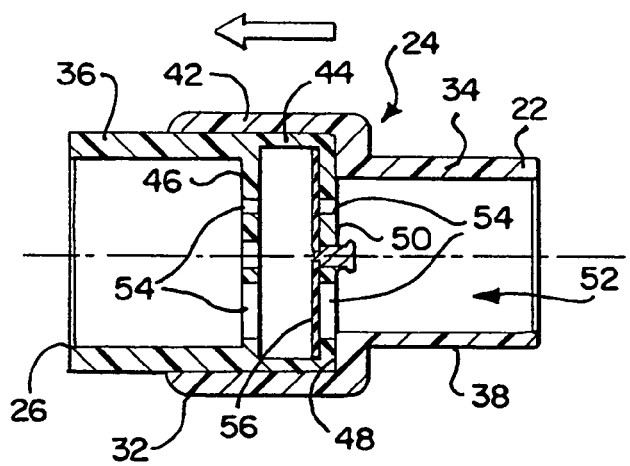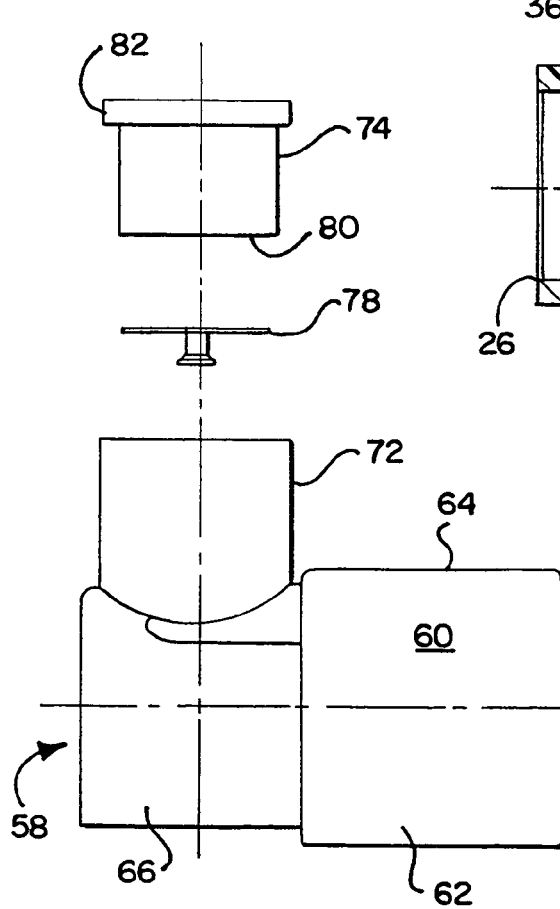

VENTILATOR CIRCUIT AND THE METHOD FOR THE USE THEREOF

This application claims the benefit of U.S. Provisional Application Ser. No. 60/446,487, filed Feb. 11, 2003, the entire disclosure of which is hereby incorporated herein by reference.

BACKGROUND

The present invention relates generally to a ventilator circuit, and in particular, to a ventilator circuit having inhalation and exhalation valves.

Patients have certain conditions that can be treated with medicaments dispensed in an aerosol and administered to the patient by inhalation. In one format, the aerosol and medicaments are contained in a container, and dispensed in metered, or measured, dosages with an inhalation device. For example, as shown in U.S. Pat. No. 6,435,177, entitled AEROSOL MEDICATION DELIVERY APPARATUS AND SYSTEM, and assigned to Trudell Medical International, the same Assignee as the present application, a holding chamber can be used to facilitate the administration of the medication to a patient. Typically, when used in a ventilation circuit, the holding chamber is introduced into the ventilation circuit just prior to the administration of the medication and is then removed.

SUMMARY

Briefly stated, in one preferred embodiment described below, a ventilator circuit for use in administering medication to a patient includes a chamber housing defining an interior space and having an input end and an output end and a one-way inhalation valve positioned upstream of the interior space. The one-way inhalation valve is operative to permit a flow of medication into the interior space of the chamber housing. An inhalation conduit communicates with the output end of the chamber and is adapted to transmit the medication to the patient. An exhaust conduit is connected to the inhalation conduit and a one-way exhaust valve is located in the exhaust conduit. The one-way exhaust valve is adapted to prevent a backflow of gas from the exhaust conduit into the inhalation conduit.

In one aspect, an adapter includes a housing having an input end adapted to be connected to the output end of the chamber, a first output end adapted to be connected to a patient interface element and a second output end adapted to be connected to an exhaust line. The housing defines first and second passageways, with the first passageway extending between the input end of the housing and the first output end of the housing. The first passageway is operative to permit the flow of gas from the output end of the chamber housing to the patient interface element. The second passageway communicates with the first passageway and a one-way exhaust valve is disposed in the second passageway.

In another aspect, a method of administering a medication to a patient includes transmitting oxygen from a gas source through a chamber and an inhalation conduit to the patient during an inhalation sequence of a breathing cycle and introducing the medication into the chamber. The method further includes preventing a substantial transmission of an exhaust gas into the chamber during an exhalation sequence of the breathing cycle and transmitting a substantial portion of the exhaust gas into the exhaust conduit during exhalation. The method further includes preventing a substantial transmission of the exhaust gas from the exhaust conduit into the inhalation conduit during subsequent inhalation sequences of the breathing cycles.

The various embodiments and aspects provide significant advantages over other ventilator circuits. In particular, the inhalation valve creates a back pressure, which prevents a substantial portion of an exhaust gas from entering the chamber. In addition, the exhaust valve also operates to prevent the exhaust gases from reentering the inhalation conduit from the exhalation conduit. In this way, the chamber can remain in the ventilator circuit even when not being used to administer a medication.

The foregoing paragraphs have been provided by way of general introduction, and are not intended to limit the scope of the following claims. The presently preferred embodiments, together with further advantages, will be best understood by reference to the following detailed description taken in conjunction with the accompanying drawings.

BRIEF DESCRIPTION OF THE DRAWINGS

FIG. 2 is a side view of an inhalation adapter.
FIG. 3 is an end view of the inhalation adapter shown in FIG. 2.
FIG. 4 is a cross-sectional view of the inhalation adapter taken along line 4-4 of FIG. 3.
FIG. 5 is an exploded side view of an exhalation adapter.

DETAILED DESCRIPTION OF THE PRESENTLY PREFERRED EMBODIMENTS

Figure 1:
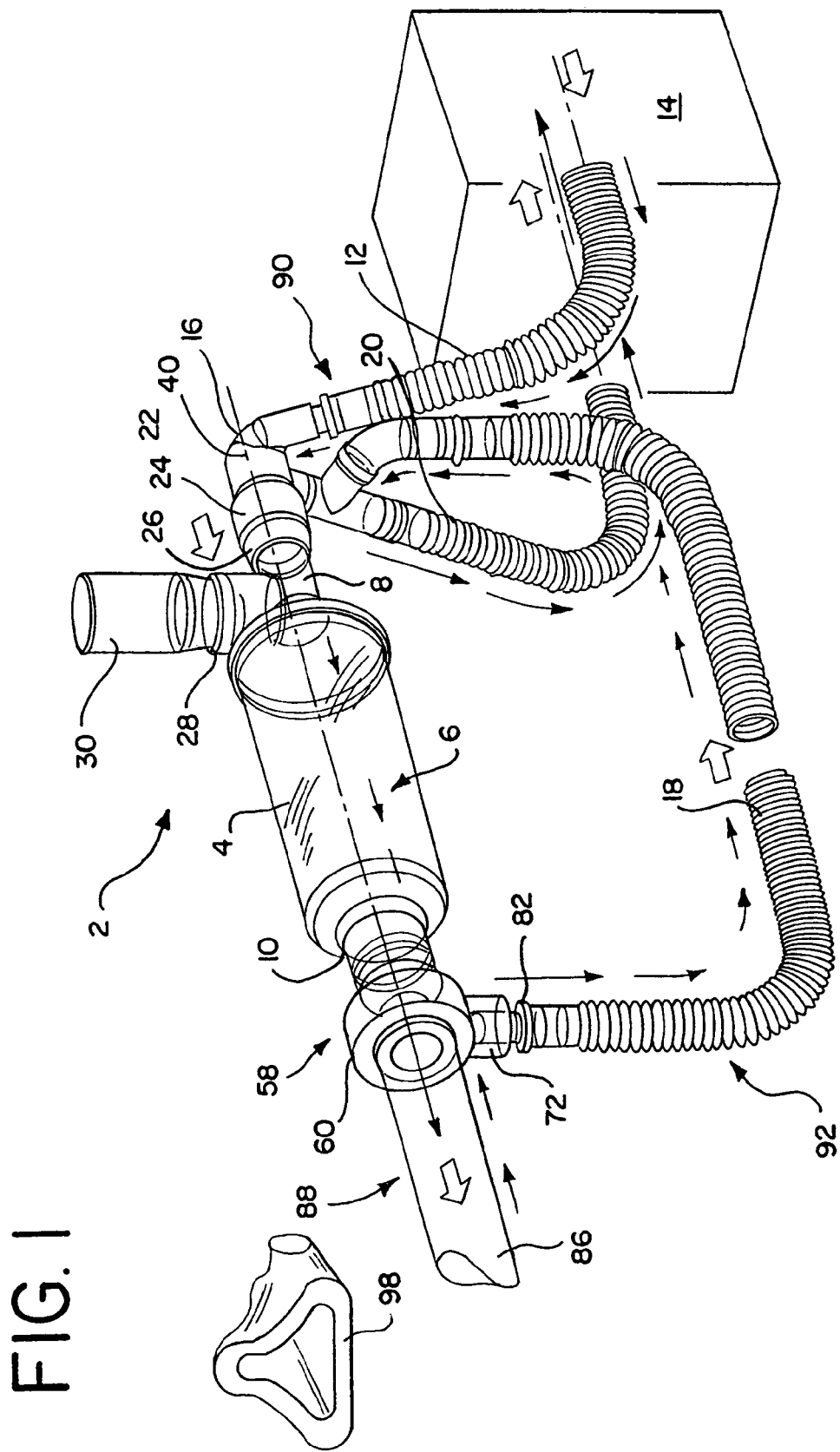
FIG. 1 is a perspective view of a ventilator circuit.
Figure 6:
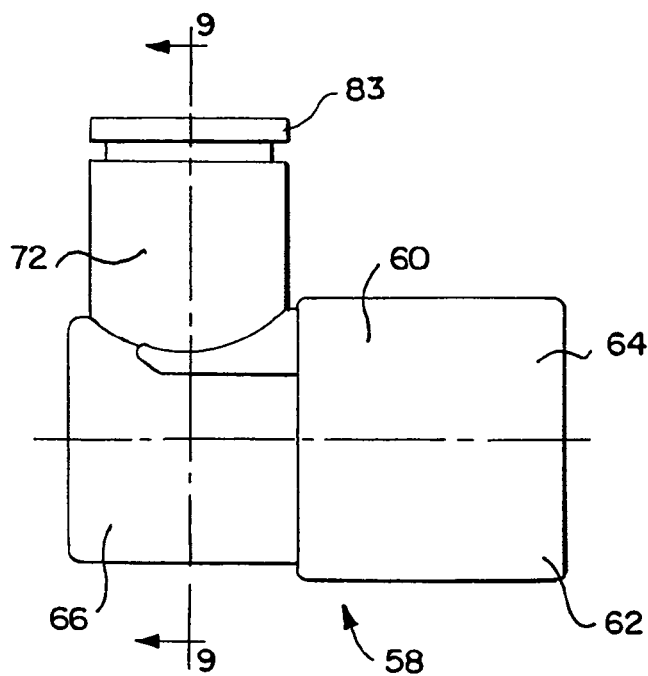
FIG. 6 is a side view of the exhalation adapter.
Figure 7:
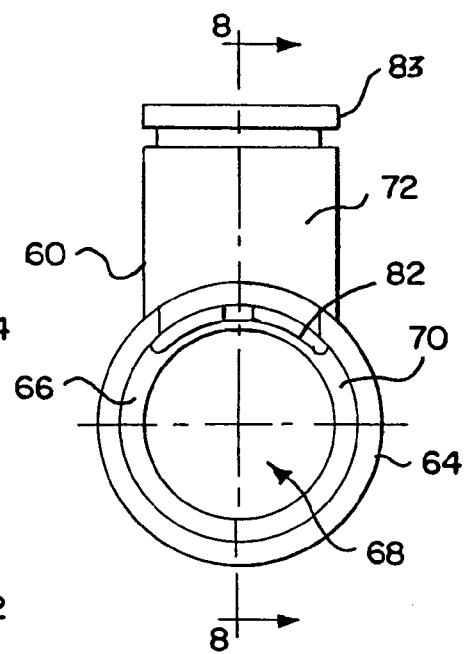
FIG. 7 is an end view of the exhalation adapter.
Figure 8:
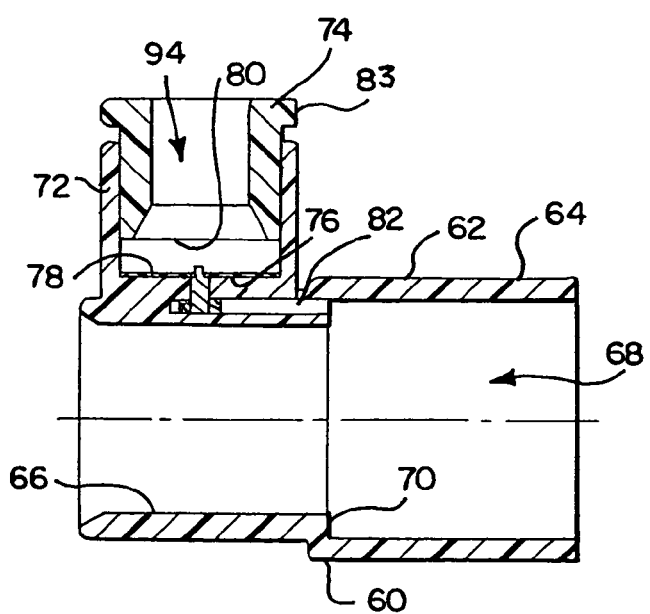
FIG. 8 is a cross-sectional view of the exhalation adapter taken along line 8-8 of FIG. 7.
Figure 9:
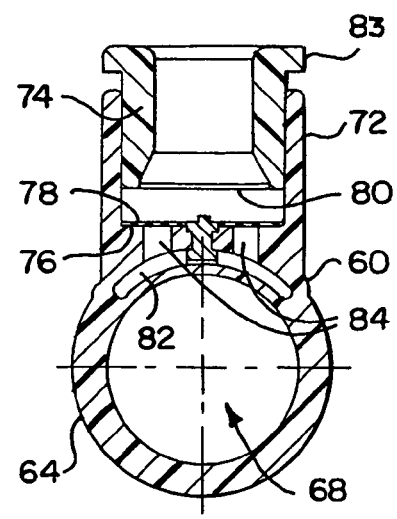
FIG. 9 is a cross-sectional view of the exhalation adapter taken along line 9-9 of FIG. 6.

Referring to FIG. 1, a ventilator circuit 2 is shown as having a holding chamber 4 positioned in the inspiratory flow path from the ventilator 14 to the patient. The holding chamber 4 has an interior space 6, an input end 8 and an output end 10. In one embodiment, the holding chamber 4, and in particular the interior space 6, preferably has a volume of between about 80 ml and 250 ml, more preferably between about 120 ml and 160 ml, and most preferably about 140 ml, although other volumes not specifically enumerated herein are suitable. Preferably, the holding chamber 4 is made of a clear plastic, although it can be non-transparent in certain embodiments. Various aspects of the holding chamber are further disclosed and described in U.S. Pat. No. 6,435,177, which is hereby incorporated herein by reference. The holding chamber 4 has a one-way inhalation valve positioned upstream of the interior space 6, and a one-way exhaust valve positioned downstream of the interior space 6. As used herein, "upstream" and "downstream" refer to the direction of the flow of gases during the inhalation sequence of a breathing cycle.

The ventilator circuit further includes a ventilator intake line 12, which forms part of an inhalation conduit 90 that runs between the ventilator and the holding chamber. The intake line 12 carries oxygen from the ventilator 14 to a WYE connector 16, which is also connected to first and second exhaust lines 18, 20. The connector 16 also is connected to an input end 22 of an inhalation adapter 24. An output end 26 of the inhalation adapter 24 is connected to the input end 8 of the holding chamber, for example by friction fit, threading or adhesive. Alternatively, the adapter can be integrally formed with the holding chamber, and in particular the input end thereof. The input end 8 of the holding chamber includes a receptacle 28 having a well shaped to receive a stem of a pressurized metered dose inhaler 30 (pMDI). The receptacle 28 is preferably positioned downstream of the inhalation valve, and is shaped and oriented to introduce medicament from the inhaler 30 into the interior space 6 of the holding chamber. It should be understood that the receptacle can be configured to connect to and support other types of medication containers or systems.

Referring to FIGS. 2-4, the inhalation adapter 24, which is disposed in and forms an additional portion of the inhalation conduit 90, includes a housing 32 formed from first and second mating components 34, 36. The first component 34 has a first cylindrical or annular portion 38 shaped to be received in an annular receptacle 40 of the WYE connector 16 and a second cylindrical or annular portion 42 extending longitudinally from the first portion 38 in a coaxial relationship therewith. The second portion 42 preferably has a greater inner diameter than the first portion 38. The second component 36 has an outer diameter dimensioned to be received in the inner diameter of the second portion 42 of the first component 34. Although the first and second components, including the various portions thereof, are shown as tubes, or tubular members, having a passageway 52 with various circular cross-sections, it should be understood that other cross-sectional shapes would also work.

A spacer member 44 is disposed between an end wall 46 of the second component 36 and a shoulder 48 formed in the first component 34 between the first and second portions 38, 42. The spacer member 44 has a valve seat 50, formed as a wall member, which extends across the passageway 52 formed through the adapter. The valve seat 50 preferably includes one or more openings 54 formed therethrough. A valve member 56 is secured to the valve seat 50 and is disposed between the valve seat 50 and the end 46 of the second component, formed in one embodiment as a wall. The end wall 46 serves as a blocking member to capture the valve member 56 in the circuit and to prevent it from passing into the holding chamber or ultimately to the patient if the valve member were to become dislodged or disconnected from the adapter. The end wall 46 also has one or more openings 54 formed therein to permit the flow of oxygen through the adapter. It should be understood that the spacer 44 could be formed integrally with the second component 36, wherein the valve seat 50 and an annular shoulder, which is spaced from the valve seat and is shaped to engage the end 46 of the first component, are formed integrally as part of the second component.

The valve member 56 and valve seat 50 function as a one-way inhalation valve. In particular, the valve member 56 is seated on the valve seat 50 and permits the flow of oxygen through the openings 54 and passageway 52 as the valve member 56 moves off of the valve seat 50 and uncovers the openings 54, but prevents the flow of gases in the opposite direction as the valve member 56 is seated on the valve seat 50 and closes the openings 54. The valve member 56 is preferably a center-post valve member. In other embodiments, the one-way inhalation valve can be configured as a duckbill valve, or other known one-way valves.

Referring to FIGS. 5-9, an exhalation adapter 58 is connected to the output end 10 of the holding chamber 4. As used herein, the terms "exhaust" and "exhalation" are interchangeable. The exhalation adapter 58 includes a housing 60 that defines in part an inhalation conduit 88, which extends between the holding chamber and the patient, and also defines in part an exhalation conduit 92. The inhalation conduits 88, 90, in combination with the interior space 6 of the holding chamber, form a complete inhalation conduit that extends between the ventilator and the patient.

The exhalation adapter housing 60 is formed from a first component 62 having a first cylindrical portion 64 and a second cylindrical portion 66 that define a passageway 68 extending therethrough. The first cylindrical or annular portion 64 has an inner diameter shaped to receive an annular or cylindrical tube extending from and defining the output end 10 of the holding chamber. Conversely, the annular portion is received inside the output end of the chamber housing. The housing 60 is preferably secured to the output end of the holding chamber 4 by friction fit, adhesives, or threading, or can be integrally molded therewith. In another embodiment, the orientation of the adapter is rotated 180 degrees.

The second cylindrical or annular portion 66 defines a channel or passageway having a lesser inner diameter, and corresponding cross-sectional area, than a channel or passageway defined by the first portion 64, so as to form an interior shoulder or annular wall 70 along the interface therebetween. The end of the tube of the output end 10 of the holding chamber, when configured in one embodiment to extend into the interior of the portion 64 rather than around the exterior thereof, is spaced from the wall 70, and is not engaged therewith such that a passageway 82 communicating through the wall 70 is not blocked by the output end.

In one preferred embodiment, the second portion 66 defines a channel having an inner diameter of between about 10 mm and 18 mm, and preferably about 15 mm, while the first portion 64 has an outer diameter of between about 17 mm and 25 mm, and preferably about 22 mm. Of course, it should be understood that other dimensions, configured to mate with various configurations of holding chambers and user interface elements, are contemplated and would be suitable therefore.

In various embodiments, the output end of the holding chamber can be configured with a narrow orifice, as disclosed in U.S. Provisional Patent Application No. 60/377,528, filed May 3, 2002 and entitled AEROSOL MEDICATION DELIVERY APPARATUS WITH NARROW ORIFICE, which is hereby incorporated by reference herein. In one embodiment, an adapter having a narrow orifice is positioned between the holding chamber and the exhalation adapter. In another embodiment, the narrow orifice is formed in the exhalation adapter. Alternatively, the narrow orifice, when formed for example in an adapter, is positioned between the portion 66 and a user interface element connected thereto. In one exemplary embodiment, the narrow orifice has a cross-sectional area of less than about 60 $mm^2$.

The housing 60 further includes a third cylindrical or annular portion 72 that extends from the second portion 66, preferably at a substantially right angle thereto, and a fourth annular portion, or connector member 74, that has an outer diameter dimensioned to be received in the inner diameter of the third portion 72. The first, second and third portions are preferably integrally formed, while the fourth portion, or connector member, is formed as a separate component. In other embodiments, all of the portions can be formed separately, or all of the portions can be integrally formed as a single unit. Although the various portions are shown as tubes, or tubular members, having passageways formed therein with circular cross-sections, it should be understood that other cross-sectional shapes would also work.

The third and fourth portions 72, 74 define a passageway 94, which in turn defines in part the exhalation conduit with the exhaust line 18. The first and second portions 64, 66, with passageway 68, define part of the inhalation conduit 88. A bottom 76 of the third portion 72, preferably formed as a wall, forms a valve seat, preferably having one or more openings formed therein. A valve member 78 is secured to the valve seat 76 and is disposed between the valve seat 76 and an end 80 of the fourth portion 74, which serves as a blocking member to capture the valve member in the circuit and prevent it from migrating upon inadvertent disconnection from the adapter. The fourth portion, or connector member 74, has an annular ring 83 at the distal end thereof that connects to an end of the exhaust line. The annular ring 83 preferably has substantially the same outer diameter as the third portion 72.

The valve member 78 and valve seat 76 function as a one-way exhalation valve. In particular, the valve member 78 is seated on the valve seat 76 and permits the flow of exhaust gases through one or more openings 84 formed in the wall 76 as the valve member 78 moves off of the valve seat 76 to expose the opening(s) 84, but prevents the flow of gases in the opposite direction as the valve member 78 is seated on the valve seat 76 and covers the openings. The valve member 78 is preferably a center-post valve member. In other embodiments, the valve can be configured as a duckbill valve, or other known one-way valves.

A passageway 82 or channel is formed in the housing 60 and connects the inhalation passageway 68 formed by the first and second portions and the exhalation passageway formed by the third and fourth portions by way of passageway 84. The passageway 82 is preferably arcuate in shape and is formed in the wall of the second portion 66. The passageway 82 opens into the passageway 68 defined by the first portion 64 through the wall 70.

A patient interface element, such as a mask 98, mouthpiece or endotracheal tube 86, is connected to the second portion 66 of the housing, for example by inserting a tubular portion thereof into the second portion, and completes the inhalation conduit 88. In other embodiments, the patient interface element is secured around the outside of the portion 66, or is formed integrally with the adapter.

It should be understood that two or more or even all of the connector 16, the inhalation adapter 24, the holding chamber 4, the exhalation adapter 58, the narrow orifice adapter (not shown), and the patient interface element 98 can be formed integrally as a single component.

In operation, and during the inhalation sequence of a breathing cycle, the ventilator 14 introduces or transmits oxygen from a gas source through the intake line 12, connector 16 and one-way inhalation valve, defined in one embodiment by the valve member 56 and valve seat 50. A user, such as a doctor or nurse, actuates the medicament container 40 by depressing the container towards the receptacle 28, which releases a metered dose of medicament into the interior space 6 of the holding chamber 4. The medicament travels with the oxygen through the output end 10 of the holding chamber 4 and through the inhalation conduit 88, formed at least in part by the passageway 68 and the patient interface element 86, 98.

During the exhalation sequence of the breathing cycle, exhaust gases are expelled from the lungs through the patient interface element 86, 98 into the exhalation adapter 58. Since the one-way inhalation valve, including in one embodiment the valve member 56 and valve seat 50 positioned upstream of the holding chamber 4, prevents the flow of gases back into the intake line, the one-way inhalation valve creates a back pressure in the holding chamber 4, thereby preventing a substantial amount of exhaust gases from entering the holding chamber 4. Instead, a substantial amount of the exhaust gases are transmitted through the passageway 82 past the one-way exhalation valve, formed in one embodiment by the valve member 78 and valve seat 76, into the passageway 94 and into the exhaust line 18. Upon the next inhalation sequence of the breathing cycle, the one-way exhalation valve prevents the exhaust gases in the exhaust line 18 from reentering the inhalation conduit 88.

Preferably, the inhalation and exhalation adapters are made of a hard plastic, including for example and without limitation ABS, polypropylene, polyethylene, metal or PVC. Preferably, the valve members are made of a flexible material, including for example and without limitation polypropylene, polyethylene, silicone, thermoplastic elastomers, EPDM, and rubber.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. A ventilator circuit for use in administering medication to a patient, the ventilator circuit comprising:
    a chamber housing defining an interior space and comprising an input end and an output end;
    a one-way inhalation valve positioned upstream of said interior space, said one-way inhalation valve operative to permit a flow of gases into said interior space of said chamber housing;
    a first inhalation conduit communicating with said output end of said chamber, said first inhalation conduit comprising an inlet communicating with said output end of said chamber housing and an outlet adapted to transmit medication to the patient, wherein said inlet and outlet are axially aligned with said output end of said holding chamber;
    a second inhalation conduit communicating with said input end of said chamber housing, wherein said one-way inhalation valve is located in said second inhalation conduit, said second inhalation conduit comprising an oxygen intake line communicating with said one-way inhalation valve, and wherein said one-way inhalation valve permits one-way flow of oxygen from said second inhalation conduit into said interior space of said chamber housing;
    an exhaust conduit communicating with said first inhalation conduit at a location positioned between said inlet and said outlet of said first inhalation conduit; and
    a one-way exhaust valve located in said exhaust conduit, said one-way exhaust valve adapted to prevent a backflow of gas from said exhaust conduit into said first inhalation conduit.

2. The ventilator circuit of claim 1 wherein said one-way inhalation valve comprises a valve member, a valve seat and a blocking member disposed in said second inhalation conduit, wherein said blocking member is spaced downstream from said valve seat, and wherein said valve member is disposed between said blocking member and said valve seat.

3. The ventilator circuit of claim 2 wherein said valve member is a center post valve member connected to said valve seat.

4. The ventilator circuit of claim 2 wherein said blocking member has at least one opening formed therein to permit the flow of gases therethrough.

5. The ventilator circuit of claim 1 wherein said first inhalation conduit comprises an endotracheal tube.

6. The ventilator circuit of claim 1 wherein said first inhalation conduit comprises a mask.

7. The ventilator circuit of claim 1 comprising an adapter connected to said output end of said chamber housing and comprising a first portion defining at least a portion of said first inhalation conduit and a second portion defining at least a portion of said exhaust conduit, wherein said one-way exhaust valve is positioned in said second portion of said adapter, and further comprising an exhaust line connected to said second portion and defining at least a portion of said exhaust conduit.

8. The ventilator circuit of claim 1 wherein said second inhalation conduit is isolated from and does not communicate with ambient air.

9. A ventilator circuit for use in administering medication to a patient, the ventilator circuit comprising:
- a chamber housing defining an interior space and comprising an input end and an output end, wherein said interior space has a first cross-sectional area defined substantially perpendicular to a longitudinal flow direction adjacent said input end;
- a one-way inhalation valve positioned upstream of said interior space, said one-way inhalation valve operative to permit a flow of gases into said interior space of said chamber housing;
- a first inhalation conduit communicating with said output end of said chamber, said first inhalation conduit adapted to transmit medication to the patient;
- a second inhalation conduit communicating with said interior space of said chamber housing at said input end, wherein said second inhalation conduit has a second cross-sectional area defined substantially perpendicular to the longitudinal flow direction at said input end, wherein said second cross-sectional area is less than said first cross-sectional area, wherein said one-way inhalation valve is located in said second inhalation conduit, said second inhalation conduit comprising an oxygen intake line communicating with said one-way inhalation valve;
- an exhaust conduit communicating with said first inhalation conduit;
- a one-way exhaust valve located in said exhaust conduit, said one-way exhaust valve adapted to prevent a backflow of gas from said exhaust conduit into said first inhalation conduit; and
- a pressurized metered dose inhaler in flow communication with said second inhalation conduit downstream of said one-way inhalation valve and upstream of said interior space of said chamber housing.

10. The ventilator circuit of claim 9 wherein said second inhalation conduit comprises an adapter having an output end connected to said input end of said chamber housing and an input end connected to said oxygen intake line, said adapter having said one-way inhalation valve disposed therein.

11. The ventilator circuit of claim 9 further comprising a WYE connector connecting said second inhalation conduit and said exhaust conduit.

12. The ventilator circuit of claim 9 wherein said oxygen intake line and said exhaust conduit are connected to a ventilator.

13. A ventilator circuit for use in administering medication to a patient, the ventilator circuit comprising:
- a chamber housing defining an interior space and comprising an input end and an output end;
- a one-way inhalation valve positioned upstream of said interior space, said one-way inhalation valve operative to permit a flow of gases into said interior space of said chamber housing;
- a first inhalation conduit communicating with said output end of said chamber, said first inhalation conduit comprising an outlet adapted to transmit medication to the patient, wherein a flow path between said interior of said chamber housing and said outlet of said first inhalation conduit through said output end of said chamber housing is free of any valve structure;
- a second inhalation conduit communicating with said input end of said chamber housing, wherein said one-way inhalation valve is located in said second inhalation conduit, said second inhalation conduit comprising an oxygen intake line communicating with said one-way inhalation valve, and wherein said one-way inhalation valve permits one-way flow of oxygen from said second inhalation conduit into said interior space of said chamber housing;
- an exhaust conduit communicating with said first inhalation conduit; and
- a one-way exhaust valve located in said exhaust conduit, said one-way exhaust valve adapted to prevent a backflow of gas from said exhaust conduit into said first inhalation conduit.

14. The ventilator circuit of claim 13 further comprising a WYE connector connecting said second inhalation conduit and said exhaust conduit.

15. The ventilator circuit of claim 13 wherein said oxygen intake line and said exhaust conduit are connected to a ventilator.

* * * * *